(12) United States Patent
Huber

(10) Patent No.: US 8,932,644 B2
(45) Date of Patent: Jan. 13, 2015

(54) COMPOSITION AND METHOD FOR CONTROL OF PLANT PATHOGENIC BACTERIA AND ENDOPHYTIC MICROORGANISMS USING SILVER PHOSPHITE

(71) Applicant: Don M. Huber, Melba, ID (US)

(72) Inventor: Don M. Huber, Melba, ID (US)

(*) Notice: Subject to any disclaimer, the term of this patent is extended or adjusted under 35 U.S.C. 154(b) by 0 days.

(21) Appl. No.: 14/321,307

(22) Filed: Jul. 1, 2014

(65) Prior Publication Data

US 2014/0315714 A1   Oct. 23, 2014

Related U.S. Application Data

(63) Continuation-in-part of application No. 12/638,824, filed on Dec. 15, 2009, now Pat. No. 8,795,736.

(51) Int. Cl.
*A01N 59/26* (2006.01)

(52) U.S. Cl.
CPC ..................................... *A01N 59/26* (2013.01)

USPC ............ 424/601; 424/604; 423/299; 423/300; 423/302; 423/304; 423/462; 423/604; 504/187; 504/188; 514/499; 514/500; 556/13; 568/8; 71/32

(58) Field of Classification Search
USPC .......... 424/601, 604; 423/299, 300, 302, 304, 423/462, 604; 504/187, 188; 514/499, 500; 556/13; 568/8; 71/32
See application file for complete search history.

(56) References Cited

U.S. PATENT DOCUMENTS 8,221,516 B1 * 7/2012 Fabry ................................ 71/32
8,585,796 B1 * 11/2013 Fabry ................................ 71/32

* cited by examiner

*Primary Examiner* — Jane C Oswecki
(74) *Attorney, Agent, or Firm* — Scott D. Swanson; Dykas & Shaver, LLP

(57) ABSTRACT

The present disclosure is directed toward a composition and method of treating and preventing infection of pathogenic microorganisms and endopyhtic microorganisms in a plant through the use of phosphite compositions.

5 Claims, No Drawings

COMPOSITION AND METHOD FOR CONTROL OF PLANT PATHOGENIC BACTERIA AND ENDOPHYTIC MICROORGANISMS USING SILVER PHOSPHITE

CLAIM TO PRIORITY

This Application claims priority to currently pending U.S. patent application Ser. No. 12/638,824, which is herein incorporated by reference.

BACKGROUND OF THE INVENTION

The invention generally relates to a composition and method for preventing and controlling bacterial infection in plants, and more particularly to preventing and controlling pathogenic bacterial infection in plants through the use of a silver phosphite compound potentially in combination with a copper-phosphite compound and/or with a nutrient-halophosphite compound.

Bacterial plant pathogens pose especially unique problems for disease control. The primary control strategy for bacterial diseases is based on exclusion of the pathogen through the use of disease free seed or propagative parts for initial planting of perennial plants or annual planting of field and vegetable crops, or quarantine and eradication if bacterial pathogens are introduced into an area. There are only a few chemical controls (antibiotics) for established bacterial diseases, and their use is limited because of phytotoxicity or pathogen mutations for resistance. Commonly applied protective copper compounds (for example sulfates or oxides) have limited benefit in controlling bacterial diseases because of their limited penetration into plant tissues where bacteria establish themselves, and mutations provide bacteria with resistance to these materials.

Unlike the control of disease outbreaks in annual crops that can be remediated in subsequent years through sanitation and the use of bacteria-free seed stocks, replanting of perennial crops such as citrus involves high capital costs to establish the planting, and several years after planting before production is initiated. Established bacterial diseases such as those caused by Candidatus *Liberibacter* species (citrus greening or Huanglongbing, psyllid yellows of tomato, or purple top and zebra chip of potatoes, etc.) that survive in alternate host plants in the environment and are disseminated by insect vectors (several species of psyllids) that commonly infect throughout the plant life cycle are very difficult to contain because of the wide dissemination range of the insect vector and long lag time for symptom expression (Bove, 2006).

Quarantine and eradication of infected plants can be as commercially damaging as the disease they are implemented to control. This was exemplified by the reintroduction of bacterial citrus canker (*Xanthomonsas citri*) to Florida in 1996 and the resulting eradication of almost 50% of commercial citrus production before the effort was abandoned in 2005 because this bacterial disease became established throughout the area by hurricanes before containment could be accomplished. Citrus canker quarantines and decontamination efforts currently limit Florida citrus markets, increase costs of production, and reduce fruit quality as effective chemical controls are not available.

The introduction and establishment of the dreaded Huanglongbing (HLB) disease (citrus greening, yellow dragon disease) caused by species of the phloem-limited bacterial pathogen, Candidatus *Liberibacter*, to Florida by 2005 has resulted in a 60-70% decline in citrus production and a serious progressive decline in tree vigor and longevity. Without effective bacterial disease control, the 2.68 billion dollar commercial citrus industry in Florida is jeopardized. The vector is present in California and other citrus producing states thus making it highly probable that this disease will soon be present throughout the United States. The lag time from infection to symptom expression for this disease varies from six months to five years depending on age of tree, vigor, and environmental factors (Bove, 2006). This lag in symptom expression provides ample time for infection before detection and containment in a new area can be accomplished.

Candidatus *Liberibacter* species infect many plant species and plug the plant's vascular (phloem) tissues to limit nutrient movement. Symptoms of this disease reflect a severe deficiency of essential mineral nutrients (for example copper, manganese, zinc). A temporary masking of symptoms can be achieved by applying high rates of foliar nutrients; however, the bacterial pathogen remains active and infected trees continue to decline in over-all vigor and productivity. Antibiotics injected into the tree's vascular system are toxic to the tree, and previously available surface-applied copper compounds are not mobile enough to inhibit bacterial activity within vascular (xylem and phloem) or other plant tissues (parenchyma, mesophyll, etc.). Current HLB control strategies of frequent insecticide sprays to limit populations of the psyllid insect vector, removal of infected trees, and nutrient maintenance to keep existing trees as productive as possible until they die provide little confidence for a sustainable citrus industry or incentive to reestablish it (Bove, 2006; UF/IFAS SWFREC, IMMOKALEE IRREC Seminar, 5 Jun. 2009).

Illustrative of the seriousness of the situation, the Florida Citrus Commission, through the Florida Citrus Advanced Technology Program (FCPRAC), has funded over $18.3 million in research the past two years to develop controls for HLB, and has announced additional funding for this year. Productive citrus acreage in Florida has declined from 1.3 million acres in 2000 to less than 500 thousand acres since the introduction of HLB, and is declining rapidly in the absence of an effective control for HLB. Few growers are willing to risk the large capital costs necessary to reestablish groves decimated by HLB until an effective disease control is available.

Another serious bacterial disease of citrus is Citrus Vareigated Chlorosis (CVC) caused by the xylem-limited *Xylella fastidiosa* bacterium. In contrast to Ca. *Liberibacter* species that inhabit the vascular phloem tissues, this bacterial pathogen causes a serious "decline, scorch, or dwarfing" disease of many other perennial fruit, nut, and forage crops by plugging the vascular xylem elements to induce a severe nutrient deficiency leading to plant decline and death.

Silver is recognized for its utility as an anti-microbial.

SUMMARY OF THE INVENTION

The present invention relates to novel compositions capable of improving plant health and facilitating the control of phytopathogenic bacteria and endophytic microorganisms within plant tissue or vascular system and to methods of applying these compositions. This relates to the essential nature of the elements as activators, inhibitors, or regulators of plant and microbial physiological processes. The embodiments of the invention described below pertain to silver-phosphite composition. embodiments and methods of using the compositions. The phosphite entity of the described embodiments of the invention facilitates absorption, translocation, and systemic distribution of the invention to contact bacteria and associated endophytic organisms in vascular and other plant tissues. Specifically the phosphite component allows for phloem mobility of the silver component to reach the endophytic bacteria located within the vascular tissues of plants. The silver entities of the described embodiments of the invention facilitate bactericidal components of the invention and/or facilitate increased plant response to bacteria and endophytic microorganism infection of a plant. Plant growth resumes following treatment of an infected plant as the damage (plugging, etc.) by the bacterium is reduced or removed and nutrient sufficiency is restored. Embodiments of the invention are anticipated to be effective against bacterial diseases of annual as well as perennial crops and ornamental plants. The present invention seeks to provide a composition that does not suffer from drawbacks of the prior art such as limited physical contact with endophytic microorganisms or bacterial tolerance to silver or related entities.

This application describes embodiments of the invention which enhance plant health by improving nutrient efficiency and/or by controlling plant associated bacteria or endophytic microorganisms without or with other inorganic plant nutrients or commercially available inorganic nutrient phosphites in amounts that produce a synergistic effect. The phosphite entity of this invention facilitates absorption, translocation, and distribution of the invention in the plant which is essential to alter the nutrition and physiology of the microenvironment colonized by pathogens and influencing the control of bacteria and endophytic microorganisms within plant tissues and the plant vascular system. It is important to note that the application of the silver phosphite is an inorganic application such that the additional nutrients or other components of the silver phosphite solution are inorganic.

The silver phosphite of an embodiment of the invention is thought to be active against silver-tolerant strains of microorganisms and to reduce the potential for silver tolerance. The silver-phosphite component may also be incorporated for this purpose with commercially available nutrient phosphites of manganese, zinc, etc., or other inorganic nutrient components. The phosphite component of the described embodiments of the invention provides the mobility to breach the bacterial-induced limitation on vascular movement to enable contact with the pathogen, serve as a synergist, and restore the plants physiological functions associated with disease resistance. Incorporation of the -silver- component with the copper phosphite of nutrient-phosphite of the invention serves a beneficial or synergistic function to enhance disease control.

Through affecting the physiological processes for plant disease inhibited, stimulated, and regulated by micronutrients, the resistance of the plant is increased and the microenvironment for microorganisms becomes less conducive for their activity or virulence. This invention is thought to facilitate the inhibition, stimulation and regulation of the critical physiological processes for plant health and disease control to promote plant health and facilitate control of bacteria and endophytic microorganisms on or in plant tissues and vascular system.

Inorganic nutrient compositions for improving plant health by facilitating the prophylactic and therapeutic control of plant pathogenic bacteria and endophytic microorganisms on or within plant tissues and vascular system such as, but not limited to, diseases caused by species of the phloem limited bacterial pathogen Candidatus *Liberibacter* species Said compositions comprising, consisting essentially of, or consisting of as active ingredients 1) silver phosphite ($Ag_2PO_3$) either without or with inorganic phosphite nutrient salts of alkali metal nutrients and beneficial elements (such as sodium, lithium, potassium), salts of ammonium, alkaline earth metal nutrients or beneficial elements (such as magnesium, calcium, barium, strontium, vanadium), or heavy metal micronutrients and beneficial elements (iron, nickel, cobalt, manganese, zinc, and aluminum) to enhance plant growth and synergize with the silver phosphite and/or copper phosphite and/or nutrient-halo phosphite, as set forth in co-pending application Ser. No. 12/638,824, for plant health and bacterial disease control. The silver phosphite and/or copper phosphite and/or nutrient-halo-phosphite (such as copper-iodo-phosphite) may be applied sequentially or simultaneously with other nutrients or nutrient phosphites in a managed plant production system to enhance plant growth and achieve bacterial disease control. The unique ingredient(s) of silver phosphite and/or copper phosphite and/or nutrient-halo-phosphite of the invention may be formulated for different application practices by using techniques available to those skilled in the art.

An embodiment of the invention is a composition for treatment of plant pathogenic bacteria and endophytic microorganisms on or within plant tissues and vascular systems. The composition has an active ingredient of silver phosphite with or without a nutrient-halo-phosphite, in particular a copper-iodo-phosphite, and/or a copper phosphite. While there can be more than one active ingredient in various embodiments of the invention, the active ingredients are generally present in a concentration that can be applied for foliar, root, or intravenous uptake within a plant and for bactericidal activity and/or plant defense stimulation within a plant. In an embodiment, the nutrient of the embodiment is selected from the group of copper, zinc, manganese, potassium, nitrogen, and iron. In another embodiment the -halo- component is an -iodo- component. Additionally, the embodiments of the invention can have inorganic components for increasing stability of the composition and/or to raise the pH of the composition. In a further embodiment, the component for increasing stability of the composition and/or to raise the pH of the composition is selected from a group of nitrogen and ammonium nitrate, both of which would be in inorganic form.

In another embodiment of the invention, the embodiment comprises a method of treating a diseased plant or preventing disease in a plant using a silver phosphite composition. The method includes the steps of assessing at least one plant for infection of the bacterial disease or for the potential infection (either immediate or in the future) of at least one plant by a bacterial disease, applying a composition comprising at least one phosphite component configured for bactericidal effect and/or a plant defense stimulation effect as an active ingredient, monitoring the plant for improvement in condition or for infection by a pathogenic bacteria or endophytic microorganism, and re-applying the composition if/as necessary for treatment of the bacterial disease within a plant or for continued prevention of a bacterial disease within the plant. In an embodiment the phosphite component is selected from a group having copper phosphite and a nutrient-halo-phosphite. The active ingredients of these compositions used in method is present in such a concentration that the composition has a plant defense stimulation effect or bactericidal effect on or within the plant. In this method, the nutrient-halo-phosphite selected from the group having the nutrients copper, zinc, manganese, potassium, nitrogen, and iron. In another embodiment, the concentration of the copper phosphite is approximately 4% in the solution used in the method. In another embodiment, the concentration of the copper phosphite is approximately 2.25%. In another embodiment the composition is formulated with nitrogen for stability and/or to change the pH of the composition. In another embodiment, the plant that is treated for disease or disease prevention is selected from the group of the perennial tree, a vine, a forage, and a herbaceous annual plant.

A further benefit to the above disclosed inventive concept (s) is that the inorganic compositions do not rely on pH as found in several of the prior art. Instead, the invention is functional across a wide range of pH values.

The purpose of the Summary of the Invention is to enable the public, and especially the scientists, engineers, and practitioners in the art who are not familiar with patent or legal terms or phraseology, to determine quickly from a cursory inspection, the nature and essence of the technical disclosure of the application. The Summary of the Invention is neither intended to define the invention of the application, which is measured by the claims, nor is it intended to be limiting as to the scope of the invention in any way.

Still other features and advantages of the claimed invention will become readily apparent to those skilled in this art from the following detailed description describing preferred embodiments of the invention, simply by way of illustration of the best mode contemplated by carrying out my invention. As will be realized, the invention is capable of modification in various obvious respects all without departing from the invention. Accordingly, the description of the preferred embodiments are to be regarded as illustrative in nature, and not as restrictive in nature.

DESCRIPTION OF THE PREFERRED EMBODIMENTS

While the invention is susceptible of various modifications and alternative constructions, certain embodiments thereof have been presented in the description and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

An embodiment of the invention is directed toward using copper phosphite to improve plant health that is impacted by plant pathogenic bacteria and endophytic microorganisms on or within plant tissues and vascular systems. A further embodiment of the invention incorporates a halide, including, but not limited to Iodine as an -iodo- component, as a beneficial component and uses the phosphite moiety as a 'carrier' to enhance absorption and systemic movement within a plant. The described embodiments of the invention efficiently provide systemic mobility of the copper phosphite and/or nutrient-halo-phosphite to suppress bacterial activity and provide plant nutrient sufficiency, with the -halo- component, such as -iodo-, as a beneficial nutrient under severe disease situations such as encountered with copper-tolerant strains of bacterial pathogens. Plant pathogenic microorganisms are difficult to control or not controllable with the current art. The current invention provides a systemic treatment for plant pathogenic microorganisms by providing a bactericidal effect while promoting plant health.

The described embodiments of the invention will work most effectively and are best suited for use in a well-managed crop production system recognizing the importance of plant health and nutritional sufficiency. The elimination of glyphosate herbicide applications can also greatly improve plant health and reduce nutrient stress and disease severity so that the invention is more effective in established disease situations. As with most plant nutrients, formulation with surfactant or adjuvant can improve ease of handling and compatibility for 'tank-mixing' with other agricultural products or chemicals. The invention can be used to efficiently provide copper or other nutrient sufficiency to plants under copper-limiting or nutrient-limiting environmental or soil situations. The invention will be less effective in improving plant health when the over-all crop production system is poorly managed.

While the concentrations of silver phosphite, potentially in conjunction with copper phosphite and/or nutrient-halophosphite can be formulated to vary depending on a wide variety of environmental conditions, it is thought that a solution having approximately 0.5%-4% silver phosphite would be beneficial. Although this number is used as an example, it is not, at filing of the application, intended to limit the application.

While nitrogen is used in various embodiments to increase stability and/or pH at higher concentrations of copper phosphite, a wide variety of stabilizers and/or components to increase pH known to those having ordinary skill in the art can be used. It is thought that using these formulations along with a regular commercial fertility program to insure nutrient sufficiency, and thus avoid deficiency, to the plants or trees, will constitute the best method of using the invention. Further, while the invention of the present application was developed with citrus plants in mind, the described embodiments of the invention are applicable to a wide variety of trees or plants and there is no intent to limit the present application to citrus trees. The exact compositions incorporating the active ingredients of the invention can vary widely but are generally known to one having ordinary skill in the art. The mixtures can further incorporate a wide variety of plant nutrients, fertilizers, and filler components.

Alternatively, varying compounds such as a nutrient-chloro-phosphite or nutrient-bromo-phosphite can be used potentially independently or in combination with manganese, zinc, potassium or similar micronutrient for bactericidal aspects as well as for increasing plant health. Additionally, the described embodiments of the invention can be practiced by adding a variety of embodiments of the invention to infected plants or to prevent infection in plants. For example, the invention can be in the form of an aqueous foliar spray, dry powder or soil treatment. In sum, the described embodiments of the invention are intended to be applied effectively to plant foliage or for root absorption and can likely be applied via injection into the plant system.

The exemplary embodiments described above illustrate but do not limit the invention. It should be understood that there is no intention to limit the invention to the specific form disclosed; rather, the invention is to cover all modifications, alternative constructions, and equivalents falling within the spirit and scope of the invention as defined in the claims. For example, while the exemplary embodiments illustrate using either copper phosphite or a nutrient-halo-phosphite, the invention is not limited to use with a composition having only one of the active ingredients. Instead, a wide variety of combinations of active ingredients can be used as well as with other active ingredients. While the invention is not limited to use with citrus plants, it is expected that various embodiments of the invention will be useful with a wide variety of plant species. Hence, the foregoing description should not be construed to limit the scope of the invention, which is defined in the following claims.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

PUBLISHED REFERENCES

Bove, J. M. 2006. Huanglongbing: a destructive, newly-emerging, century-old disease of citrus. Journal of Plant Pathology 88:7-37.
Datnoff, L. E., W. H. Elmer, and D. M. Huber. 2009. Mineral Nutrition and Plant Disease. APS Press, St. Paul, Minn.
Evans, I., E. Solberg, and D. M. Huber. 2007. Copper and plant disease. Chapter 12. In: L. E. Datnoff, W. H. Elmer, and D. M. Huber (eds.). Mineral Nutrition and Plant Disease. APS Press, St. Paul, Minn.
Huber, D. M. 1978. Disturbed mineral nutrition. In: J. G. Horsfall and E. B. Cowling (eds), Plant Disease, An Advanced Treatise, Volume 3, *How Plants Suffer from Disease*. Academic Press, NY.
Huber, D. M. 1980. The role of mineral nutrition in defense. In: J. G. Horsfall and E. B. Cowling (eds), Plant Disease, An Advanced Treatise, Volume 5, *How Plants Defend Themselves*. Academic Press, NY.
Huber, D. M. and R. D. Graham. 1999. The role of nutrition in crop resistance and tolerance to diseases. In: Z. Rengel (ed.), Mineral Nutrition of Crops. Food Products Press, London.
Johal, G. and D. M. Huber. 2009. Glyphosate effects on diseases of plants. European Journal of Agronomy 31 (3): 144-152.

The invention claimed is:

1. A method of controlling bacterial infection in plants using an inorganic phosphite composition, said method consisting of the steps of:
  assessing at least one plant for infection of said plant by a bacterial disease;
  applying said inorganic phosphite composition if said plant is infected by a bacterial disease to said plant infected by a bacterial disease, said inorganic phosphite composition consisting of at least one inorganic phosphite component configured for bactericidal effect and/or a plant defense stimulation effect as an active ingredient, wherein said at least one inorganic phosphite component is silver phosphite, wherein said active ingredient is present in such a concentration that said inorganic phosphite composition is configured to have a plant defense stimulation effect or a bactericidal effect on or within said plant; and at least one inorganic phosphite component further optionally consisting of sodium, lithium, potassium, salts of ammonium, alkaline earth metal nutrients, magnesium, calcium, barium, strontium, iron, nickel, cobalt, manganese, zinc or aluminum,
  monitoring said plant for improvement in condition and/or for infection by a bacterial disease; and
  reapplying said inorganic phosphite composition if necessary for treatment of a bacterial disease within a plant;
  with the caveat that the inorganic phosphite composition contains no organic components.

2. The method of controlling bacterial infection in plants using an inorganic phosphite composition of claim 1, wherein said at least one inorganic component further consists of sodium, lithium, potassium, salts of ammonium, alkaline earth metal nutrients, magnesium, calcium, barium, strontium, iron, nickel, cobalt, manganese, zinc, aluminum, or other inorganic fertilizer.

3. The method of controlling bacterial infection in plants using an inorganic phosphite composition of claim 1, wherein said step of assessing at least one plant for a bacterial disease comprises assessing at least one plant selected from the group consisting of a perennial tree, a vine, a forage and a herbaceous annual plant for a bacterial disease.

4. A method of controlling bacterial infection in plants using an inorganic phosphite composition, said method consisting of the steps of:
  assessing at least one plant for infection of said plant by a bacterial disease;
  applying an inorganic phosphite composition if said plant is infected by a bacterial disease to said plant infected by a bacterial disease, wherein said inorganic phosphite composition consists essentially of at least one inorganic phosphite component configured for bactericidal effect and/or a plant defense stimulation effect as an active ingredient, wherein said at least one inorganic phosphite component is inorganic silver phosphite, wherein said active ingredient is present in such a concentration that said inorganic phosphite composition is configured to have a plant defense stimulation effect or a bactericidal effect on or within said plant;
  monitoring said plant for improvement in condition and/or for infection by a bacterial disease; and
  reapplying said inorganic phosphite composition if necessary for treatment of a bacterial disease within a plant,
with the caveat that the inorganic phosphite composition contains no organic components.

5. The method of claim 4, wherein said method further consists of applying inorganic copper phosphite and/or inorganic nutrient-halo-phosphite with the silver phosphite.

* * * * *